United States Patent [19]

Opsal

[11] Patent Number: 5,074,669
[45] Date of Patent: Dec. 24, 1991

[54] METHOD AND APPARATUS FOR EVALUATING ION IMPLANT DOSAGE LEVELS IN SEMICONDUCTORS

[75] Inventor: Jon Opsal, Livermore, Calif.
[73] Assignee: Therma-Wave, Inc., Fremont, Calif.
[21] Appl. No.: 448,882
[22] Filed: Dec. 12, 1989
[51] Int. Cl.$^5$ ............................................. G01N 21/55
[52] U.S. Cl. ..................................... 356/445; 356/432
[58] Field of Search ................ 356/445, 432, 400, 300, 356/71; 374/5, 57

[56] References Cited

U.S. PATENT DOCUMENTS 4,579,463 4/1986 Rosencwaig et al. ............... 356/445
4,755,049 7/1988 Bomback et al. .

Primary Examiner—Richard A. Rosenberger
Assistant Examiner—LaCharles P. Keesee, II
Attorney, Agent, or Firm—Limbach, Limbach & Sutton

[57] ABSTRACT

An apparatus (10) designed to evaluate ion implantation levels in semiconductor samples (42) is disclosed. The device includes an intensity modulated pump laser beam (22) and a probe beam (62) having a different wavelength than the pump beam. The two laser beams are focused on a coincident spot on the surface of the sample. Detectors (80, 96) are provided for measuring the non-modulated reflected power of the pump and probe beams. In addition, the modulated reflected power of the probe beam, that is in phase with the intensity modulated pump beam, is also measured. These three independent measurements are utilized to derive the implant dosage level in the semiconductor sample.

10 Claims, 2 Drawing Sheets

METHOD AND APPARATUS FOR EVALUATING ION IMPLANT DOSAGE LEVELS IN SEMICONDUCTORS

TECHNICAL FIELD

The subject apparatus is for evaluating the ion implant dosage level in semiconductor samples. The apparatus is particularly suited for evaluating samples having high dosage levels.

BACKGROUND OF THE INVENTION

Most semiconductor fabrication techniques include one or more ion implantation process steps. In order to maintain high yields, the ion implantation must be accurately controlled. A number of different approaches have been developed for measuring the dosage level in a semiconductor sample. One particularly advantageous approach is based upon the measurement of a modulated reflectance signal which can be related to the dosage level.

A modulated reflectance signal is obtained by periodically exciting the semiconductor sample with a focused, intensity modulated, pump laser beam. A probe beam is then reflected off the surface of the sample within the periodically excited area. The reflected power of the probe beam is measured to yield the modulated reflectance signal. This measurement is then correlated with the dosage level.

The above described approach provides a high resolution, non-contact technique. This technique is described in greater detail in U.S. Pat. No. 4,636,088 issued Jan. 13, 1987 and U.S. Pat. No. 4,854,710 issued Aug. 8, 1989 both assigned to the same assignee as the subject invention. As described therein, the modulated reflectance signal is effected by the presence of both thermal and plasma waves in the semiconductor sample.

The techniques described in the latter patents have been incorporated in a device manufactured by Therma-Wave, Inc. of Fremont, Calif. and marketed under the trademark Therma-Probe. The Therma-Probe device is being widely used by the semiconductor industry to monitor all types of ion implant processes. Up until now, this device has been limited to monitoring dosage levels up to $10^{14}$ to $10^{15}$ ions/cm$^2$. Some semiconductor manufacturers are now using higher doses, up to $10^{16}$ ions/cm$^2$.

The difficulty in extending the sensitivity of the device to the highest dosage levels is due principally to the fact that the rise in the measured modulated reflectance signal, which is monotonic below $10^{14}$ ions/cm$^2$ and can therefore be directly correlated with dosage level, becomes oscillatory at higher dosage levels. The reason for this change in behavior in the modulated reflected signal has been attributed to the fact that the high level of ion implantation transforms the crystalline material into amorphous silicon. Amorphous silicon is created when more than ten percent of the atoms in the lattice structure are displaced. Amorphous silicon is characterized by the fact that no x-ray diffraction patterns can be generated since the lattice has been so severely disturbed.

Typically, a layer of amorphous silicon is created which lies just below an upper layer of less damaged silicon. The reason there is a layer of damaged (but still crystalline) silicon above the amorphous silicon layer depends upon the type of ions which are being implanted. For example, implantation using the arsenic ion requires relatively high energies. Some of this implantation energy is transferred to the material near the upper surface of the sample creating a dynamic annealing effect which recreates the crystalline structure. A different scenario occurs in boron implantation. More specifically, the boron ions are implanted with very high speed and literally pass through the upper layer before they have slowed down enough to interact with the lattice in an amount sufficient to create amorphous silicon. In either case, the result of high dosage implantation is to create an upper layer of damaged, crystalline silicon and an intermediate layer of amorphous silicon below.

The significance of the presence of the amorphous silicon layer is that this layer acts as a boundary which can reflect optical radiation. This reflection gives rise to interference effects which, in turn, effect the response of the modulated reflectance signal. This theoretical explanation was first described by the applicant herein in "Modulated Interference Effects and Thermal Wave Monitoring of High Dose Implantation in Semiconductors," *Review of Progress in Quantitative Non-destructive Evaluation*, Vol. 8B, 1989.

The latter article also describes how the thickness of the amorphous silicon layer can be related to the level of ion implantation. More specifically, as the level of ion implantation increases to high dosages, the thickness of the amorphous silicon layer will increase. The latter article also includes calculations indicating how both the modulated and non-modulated reflectance signals of a probe beam will behave as the thickness of the amorphous silicon layer increases. [See also "Modulated Optical Reflectance Measurements on Amorphous Silicon Layers and Detection of Residual Defects", S. Wurm, P. Alpern, D. Savignac, and R. Kakoschke, Appl. Phys. A 47, 147-155 (1988).]

The effects of the presence of an amorphous silicon layer on surface reflectivity was further discussed by the applicant in "High Resolution Thermal Wave Measurements and Imaging of Defects and Damage on Electronic Materials", J. Opsal, which was first presented in August 1989 and will appear in *Photoacoustics and Photothermal Phenomena* VI (Springer-Verlag 1990). The latter paper discusses how the reflectivity of a sample which has been implanted with a high level of ions could be analyzed using a general mathematical model of a multi-layer system. This approach provides a mathematical framework for relating the reflectivity of a sample to the thickness of the amorphous silicon layer. As noted above, the thickness of the amorphous silicon layer is related to the dosage level. Therefore, if one can determine the thickness of the amorphous silicon layer, the dosage level in the sample can be evaluated.

Unfortunately, simply setting forth a general mathematical model which defines the reflectivity response of a layered sample does not alone permit the calculation of the thickness of the amorphous silicon layer based on the measurement of the modulated reflectivity signal. More particularly, a typical implanted semiconductor sample consists of a number of layers each having an unknown thickness. As noted above, a typical sample includes an upper damaged crystalline layer and a lower layer of amorphous silicon. In addition, there is typically an upper mask layer formed from an oxide material. The thickness of all three layers is unknown, and thus a single measurement of the modulated reflectance signal cannot be used to solve multiple equations in a mathematical model which includes unknown values for three layer thicknesses.

SUMMARY OF THE INVENTION

In order to overcome the problems described above and to permit the calculation of the thickness of the amorphous silicon layer and then evaluate the dosage level, the subject apparatus and method provides for the measurement of three independent reflectivities. The first measurement is defined by the above described modulated reflectance signal of a probe beam. The second measurement is of the non-modulated reflectance signal of the probe beam. The third measurement is defined by the non-modulated reflectance of a separate beam, having a wavelength different than the probe beam. These three independent measurements can be used in conjunction with a mathematical model to calculate the thickness of all the unknown layers, including the thickness of the amorphous silicon layer. Once the thickness of the amorphous silicon layer is derived, the dosage level can be determined through calibration techniques.

The principal components of the subject apparatus are similar to those found in the above mentioned Therma-Probe device and described in the above cited patents which discuss the measurement of thermal and plasma waves in semiconductors. The principal difference is that the measurements which can be obtained are now utilized in a novel manner to produce a new result not heretofore disclosed or contemplated.

As described in the above-identified patents, the subject apparatus includes an intensity modulated pump laser for exciting the semiconductor sample. A probe beam having a different wavelength than the pump beam is focussed with the pump beam to a substantially coincident spot on the surface of the sample. A first photodetector is providing for measuring the modulated reflected power of the probe beam. The modulated reflected power is based on the signal which is in phase with the intensity modulated pump beam. The second independent measurement taken is the non-modulated reflected power of the probe beam. As will be described in detail below, this second measurement can be made using the same photodetector element which measured the modulated reflected power of the probe beam. In accordance with the subject invention, a third independent reflectivity measurement is also made. This third reflectance signal consists of the non-modulated power of the pump beam. A separate photodetector is used for this purpose. As noted above, these three independent measurements can be used to evaluate the dosage level in the semiconductor sample.

In the prior art Therma-Probe device, the nonmodulated reflected power of both the pump and probe beams have been measured. These measurements were taken in order to normalize the modulated reflectance signal. More specifically, the non-modulated pump and probe beam reflected powers must be measured to normalize the modulated probe beam reflectance signal so that any effects of absorption of the pump and probe beam wavelengths in the sample can be cancelled. In certain models of the prior art Therma-Probe device, the non-modulated reflected power of the pump beam is also used to help locate areas of interest on the semiconductor sample. This approach is described in U.S. Pat. No. 4,795,260 issued Jan. 3, 1989 and also assigned to the assignee of the subject invention. While the non-modulated reflective pump and probe beam powers have been measured and utilized in the prior art, there has never been any effort to utilize those measurements in combination to derive information about ion implantation levels as described in greater detail below.

DETAILED DESCRIPTION OF THE PREFERRED EMBODIMENT

Figure 1:
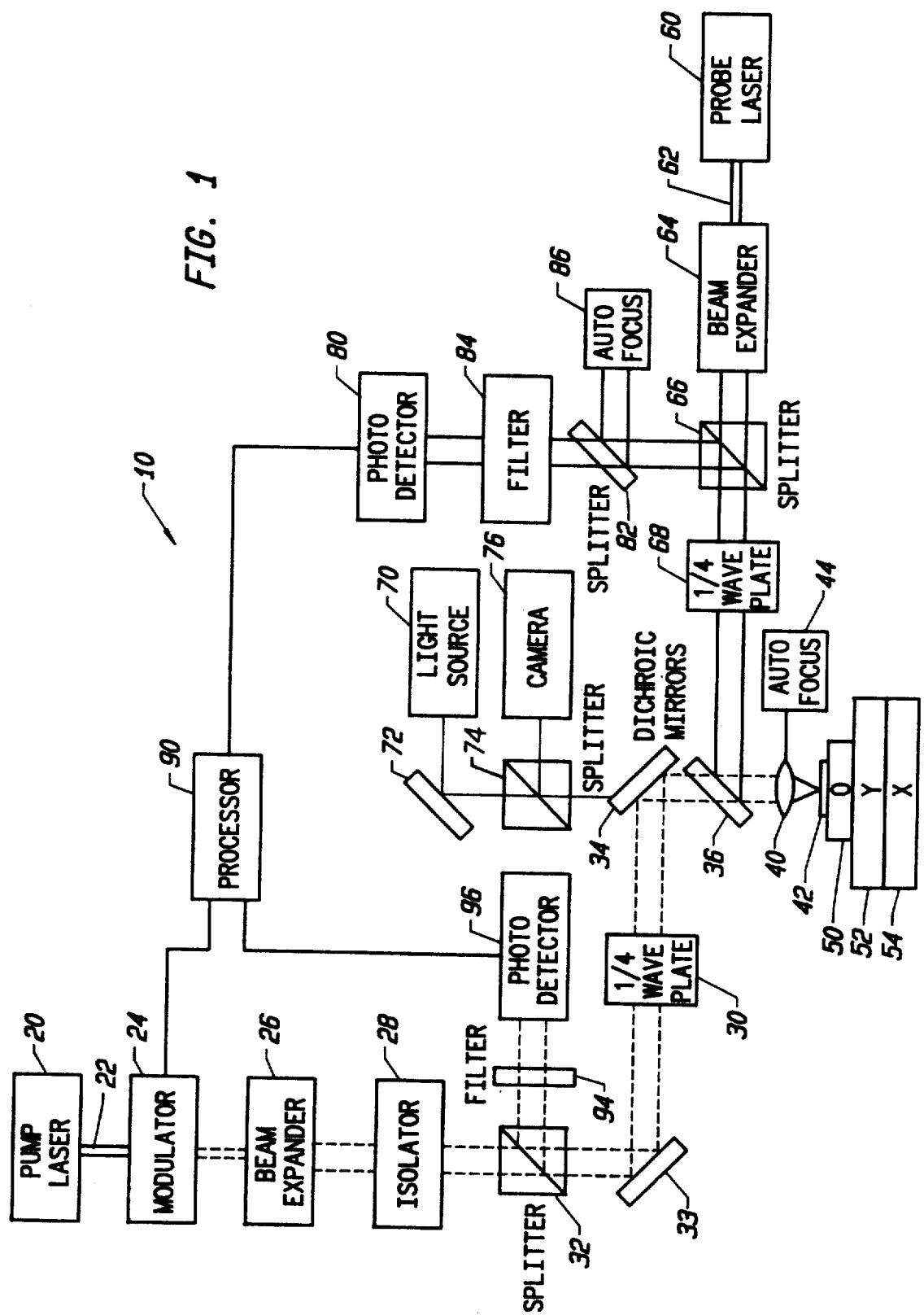
FIG. 1 is a block diagram of the subject invention.

Turning to FIG. 1, there is illustrated an apparatus 10 designed to measure the dosage level in semiconductors based on the surface reflectivity of the sample. The device 10 includes a pump laser 20 which may be an argon laser with a 488 nm, 35 Mw output beam 22. An acousto-optic modulator 24 is provided for intensity modulating the output beam 22 of pump laser 20. In the preferred embodiment, the modulation frequency is on the order of 1-10 MHz.

The intensity modulated beam 22 is then passed through a beam expander 26 and an isolator 28 for preventing feedback into the pump laser cavity. The beam then passes through splitter 32 discussed below. A turning mirror 34 is illustrated for convenience.

The beam 22 is then passed through a quarter waveplate optical rotator 30. A dichroic mirror which reflects the argon radiation 34 is then used to redirect the beam downwardly through a second dichroic mirror 36 which is transparent to the argon radiation. The beam is then focussed by a microscope objective 40 onto the surface of a semiconductor sample 42 with an incident power of about 10 mW. An autofocus mechanism 44 is provided to maintain a spot size resolution of about 1 micron in diameter. The intensity modulated pump laser beam functions to periodically excite the sample creating plasma and thermal waves.

The sample rests on a movable stage. The upper stage level 50 provides rotation about an angle $\theta$ and the lower two stages 52 and 54 provide x and y motion respectively.

The subject apparatus 10 further includes a probe laser 60 for emitting a beam 62. Probe laser 60 is preferably a linearly polarized helium neon laser generating a 633 nm beam 62 having a 5 mW power output. Beam 62 is passed through a beam expander 64 and a splitter element 66. The beam is then passed through a quarter waveplate 68 and is reflected downwardly to the sample surface by dichroic mirror 36 with an incident power of about 3 mW. The pump and probe beams are focussed in a substantially coincident manner on the surface of the sample to maximize the reflectivity signal.

In the preferred embodiment, a vision system is provided to help view the sample. The vision system includes a white light source 70 which is directed to the sample by turning mirror 72 through a splitter 74 and through the dichroic mirrors 34 and 36. The returning light is redirected by the splitter 74 to a camera 76.

In accordance with the subject invention, three independent reflectivity measurements are made in order to derive information about the ion implantation dosage level of the sample 42. These measurements include the modulated and non-modulated reflected power of the probe beam 62 as well as the non-modulated reflected power of the pump beam 22. The elements utilized to obtain these measurements are disclosed below.

As illustrated in FIG. 1, the reflected probe beam is redirected by mirror 36 through quarter waveplate 68. The second pass through the quarter waveplate 68 functions to rotate the polarization of the beam a full 90° so that when the beam reaches splitter 66 it is redirected upwardly towards photodetector 80. Prior to reaching photodetector 80, the reflected probe beam 62 will pass through a splitter 82 and an isolation filter 84. Isolation filter 84 is designed to shield photodetector 80 from any stray argon pump radiation. Splitter 82 functions to pick off a small portion of the beam and redirect it to an autofocus mechanism 86.

Photodetector 80 is designed to measure the reflected power of the probe beam. This result is achieved by making sure that the probe beam underfills the surface of the photodetector. In this manner, photodetector 80 measures only the modulations in the reflected power and is insensitive to any small variations in probe beam diameter or position that are induced by thermal lens effects or thermo-elastic deformations at the sample surface. The photodetector functions to generate a voltage proportional to the power of the beam falling on its surface. This signal is then supplied to a processor 90. The DC component of the voltage signal supplied to the processor defines the non-modulated probe beam reflectance. Processor 90 is connected to modulator 24 so that a phase-sensitive synchronous detection system can be used to measure modulated reflectance changes at 1-10 Mhz frequencies as small as $10^{-7}/\sqrt{Hz}$. As can be appreciated, the output from photodetector 80 is used by the processor to derive both the modulated and non-modulated reflected powers of the probe beam.

The third remaining independent reflectivity measurement is of the non-modulated pump beam power. As illustrated in FIG. 1, the reflected pump beam 22 is redirected back through quarterwaveplate 30 by dichroic mirror 34. The second pass through the quarter waveplate 30 functions to rotate the polarization of the beam a full 90° so that the bulk of the reflected pump power can be reflected out of the system by isolator 28. Splitter 32 is provided to pick-off a small portion (approximately 4%) of the reflected pump beam radiation. This pump beam radiation is passed through a filter 94 for isolating the helium neon probe radiation prior to reaching detector 96. The pump beam is arranged to underfill the surface of photodetector 96 for the reasons discussed above. The output voltage from detector 96 is supplied to processor 90 and the DC component of that voltage is used to derive the non-modulated power of the reflected pump beam.

In the preferred embodiment, two additional photodetectors and optical pick-offs (not shown) are provided for measuring the incident powers of the pump and probe beams. The incident beam power is measured to correct for variations in the power of the lasers.

Figure 2:
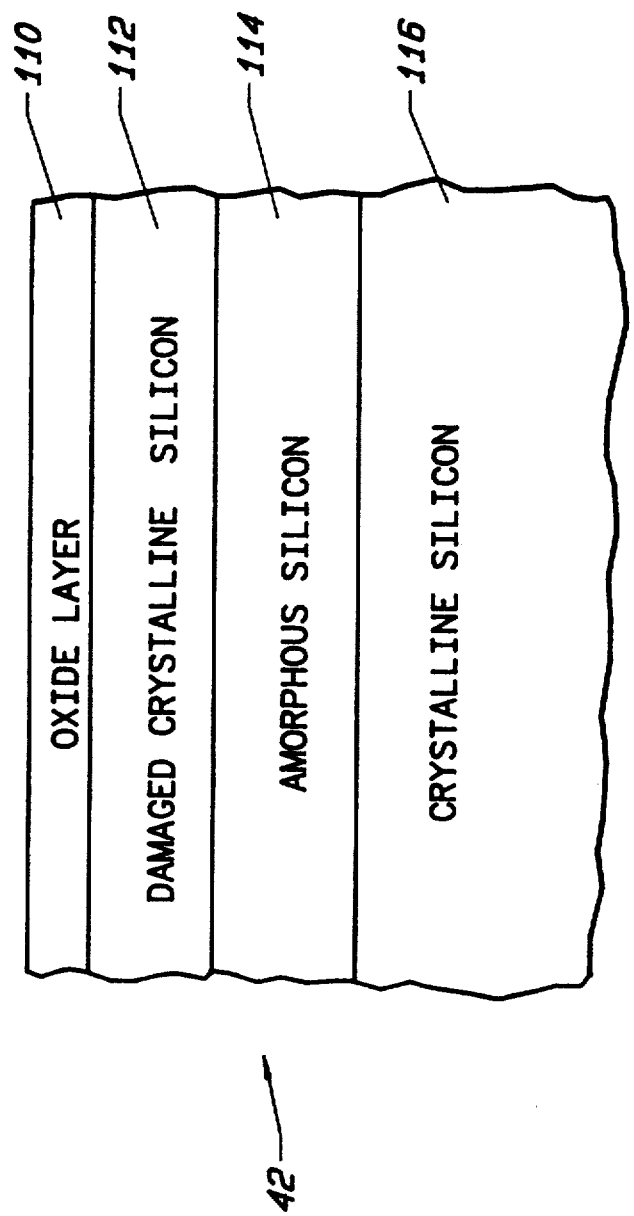
FIG. 2 is a cross-sectional, schematic view of a sample semiconductor.

Using the three measured reflectance signals, the processor can then determine the thickness of the amorphous silicon layer which, in turn, can be related to the dosage level in the sample. The mathematical approach can best be understood by referring to FIG. 2 which shows a cross-section of the upper surface of a semiconductor sample 42. As shown in FIG. 2, the upper surface of the sample includes a thin oxide layer 110. Just below the oxide layer is a layer 112 of damaged crystalline silicon. Below that crystalline layer is a layer of amorphous silicon 114. The remainder of the sample is shown as 116. As noted above, the thickness of each of the layers 110, 112, and 114 is unknown. However, a mathematical model can be developed which relates the reflectivity of the sample to the thickness of these layers using well-known Fresnel equations. The equations which are utilized for this specific approach are set forth below.

In any layer of a system of M layers, one can derive the following recursion relation on the complex reflection coefficient $\rho_n$, $$\rho_n = \left( \frac{r_n + \rho_{n+1}}{1 + r_n \rho_{n+1}} \right) e^{2ik_n d_n} \quad (1)$$

valid for $0 \leq n < M+1$ with the initial substrate condition $\rho_{M+1} = 0$. In Eq. (1) $r_n$ is a characteristic reflection coefficient defined by $$r_n = \frac{k_{n+1} - k_n}{k_{n+1} + k_n}$$

where $k_n$ is the optical wave vector $$k_n = \frac{2\pi}{\lambda} (N_n + iK_n)$$

$\lambda$ is the probe beam wavelength and $d_n$ is the thickness of the $n^{th}$ layer and where $N_n$ and $K_n$ are, respectively, the real and imaginary parts of the complex refractive index. The reflectance R is simply the square of the magnitude of $\rho_o$.

By differentiating Eq. (1) and assuming that any thermal or plasma wave effects are slowly varying on an optical scale we have the following expression for the modulation of the complex reflection coefficient at the front surface of the sample, $$\Delta\rho_o = \frac{1}{2} \sum_{n=1}^{M+1} w_n (1 - \rho_n^2) \left( \frac{\Delta k_n}{k_n} - \frac{\Delta k_{n-1}}{k_{n-1}} \right) + \quad (2)$$

$$2i \sum_{n=0}^{m} w_n k_n \rho_n \int_{x_{n-1}}^{x_n} dx \frac{\Delta k_n}{k_n} + 2i \sum_{n=0}^{M} w_n \dot{i} n \rho_n \Delta d_n$$

where the $w_n$ are optical weighting coefficients that satisfy the recursion relation, $$w_{n+1} = w_n \left( \frac{1 + r_n^2}{(1 + r_n \rho_{n+1})^2} \right) e^{2ik_n d_n}$$

which is valid of $0 \leq n < M$ with the initial condition $w_o = 1$ and formally setting $d_o = 0$ and $x_{-1} = -\infty$. The first term in Eq. (2) describes the modulation in the optical contrast at the layer boundaries. The second term is essentially the thermal lens effect known to occur anywhere in which there is a gradient in the optical properties of the material. The last term describes the effect of modulating the layer thickness either through thermal or plasma wave-induced expansion. The modulation of the reflectance $\Delta R$ is obtained by taking twice the real part of $\Delta \rho_o$.

The above equations can be solved for three unknown layer thicknesses (M=3) if at least three independent measurements are taken. More specifically, each individual measurement will generate a group of possible solutions for the various layer thicknesses. The optimum solution for the thickness of the three unknown layers can be derived with a straight-forward least squares fitting technique. As noted above, if the thickness of the amorphous silicon layer is calculated, the dosage level can be derived.

The actual dosage level of the sample is derived through calibration techniques. In practice, a plurality of test wafers are manufactured having various known dosage levels such as $10^{15}$, $2 \times 10^{15}$, $5 \times 10^{15}$ and $10^{16}$ ions/cm$^2$. The measurements described above are taken on the test wafers. These measurements are used to calculate the thickness of the amorphous silicon layers formed in the test wafers. In practice, it has been found that the thickness of the amorphous silicon layer is roughly proportional to the $\sqrt{\log \text{Dose}}$.

After the calibration has been completed, actual samples can be evaluated. As noted above, the reflectivities of the actual samples are measured and the thickness of the amorphous silicon layer is calculated. This calculated layer thickness is compared with the calculated thickness of the test wafers so that the dosage level can be derived.

The above described approach has been used to measure arsenic and phosphorous dosage levels between $10^{14}$ ions/cm$^2$ and $10^{16}$ ions/cm$^2$. In practice, it has been found that this approach can also be used to enhance the accuracy of the measurement of dosage levels below $10^{14}$ ions/cm$^2$ which are insufficient to create a layer of amorphous silicon. More specifically, it has been found that the non-modulated reflected power signals from the probe and pump beams will begin to show some dependence on dose as the dosage level reaches about $10^{13}$ ions/cm$^2$. Thus, at doses below the amorphization threshold (e.g., $10^{14}$ arsenic ions/cm$^2$) we can assume a damaged silicon layer with a thickness dependent only on the energy of the implanted ions but with optical properties that can be calibrated against dose variation. More specifically, for any given constant energy ion implantation process, the thickness of the ion-implantation-induced damaged layer is fixed in the model and the optical properties of the damaged layer are allowed to increase monotonically with dose over a range of values bounded by those of crystalline silicon and amorphous silicon.

While the subject invention has been described with reference to a preferred embodiment, various changes and modifications could be made therein by one skilled in the art without varying from the scope or spirit of the subject invention as defined by the appended claims. For example, the subject approach can also be used to determine implant dosage levels of non-silicon based semiconductors such as the more recently developed gallium-arsenic semiconductors.

I claim:

1. An apparatus for evaluating the implant dosage level of a semiconductor sample having an oxide surface coating comprising:

means for emitting an intensity modulated pump beam of radiation;

means for emitting a probe beam of radiation having a different wavelength than the pump beam of radiation;

means for focusing the pump and probe beams at a substantially coincident spot on the surface of the sample;

means for measuring the modulated reflected power of the probe beam that is in phase with the intensity modulated pump beam;

means for measuring the nonmodulated reflected power of the probe beam;

means for measuring the nonmodulated power of the reflected pump beam; and means for processing the three reflected power measurements to evaluate the implant dosage level in the semiconductor sample.

2. An apparatus as recited in claim 1 wherein said processor utilizes the reflected power measurements to calculate the thickness of a material layer created by the implantation and wherein the thickness of the material layer is correlated to the dosage level.

3. An apparatus for evaluating the implant dosage level of a semiconductor sample having an oxide surface coating and an internal amorphous material layer created by a high dosage level comprising:

means for emitting an intensity modulated pump beam of radiation;

means for emitting a probe beam of radiation having a different wavelength than the pump beam of radiation;

means for focusing the pump and probe beams at a substantially coincident spot on the surface of the sample;

first detector means for measuring the power of the reflected probe beam, said first detector means for measuring the modulated reflected power of the probe beam that is in phase with the intensity modulated pump beam, said first detector means for also measuring nonmodulated reflected power of the probe beam.

second detector means for measuring the nonmodulated power of the reflected pump beam; and means for processing the three reflected power measurements obtained by the first and second detector means to derive the thickness of the amorphous material layer and thereafter correlating the derived thickness of the amorphous material layer to the implant dosage level in the semiconductor sample.

4. An apparatus as recited in claim 3 wherein said processor compares the derived thickness of the amorphous material layer to the derived thickness of the amorphous material layer of other semiconductor samples having a known implant dosage level.

5. An apparatus as recited in claim 3 wherein said semiconductor sample is formed from crystalline silicon and the amorphous material layer is amorphous silicon.

6. A method for evaluating the implant dosage level of a semiconductor sample having an oxide surface coating, said method comprising the steps of:

generating an intensity modulated pump beam of radiation;

generating a probe beam of radiation having a different wavelength than the pump beam of radiation;

focusing the pump and probe beams at a substantially coincident spot on the surface of the sample;

measuring the modulated reflected power of the probe beam that is in phase with the intensity modulated pump beam;

measuring the nonmodulated reflected power of the probe beam;

measuring the nonmodulated power of the reflected pump beam; and processing the three reflected power measurements to evaluate the implant dosage level in the semiconductor sample.

7. A method as recited in claim 6 wherein said processing step includes calculating the thickness of a material layer created by the implantation and wherein the thickness of the material layer is correlated to the dosage level.

8. A method for evaluating the implant dosage level of a semiconductor sample having an oxide surface coating and an internal amorphous material layer, said method comprising the steps of:

generating an intensity modulated pump beam of radiation;

generating a probe beam of radiation having a different wavelength than the pump beam of radiation;

focusing the pump and probe beams at a substantially coincident spot on the surface of the sample;

measuring the modulated reflected power of the probe beam that is in phase with the intensity modulated pump beam;

measuring the nonmodulated reflected power of the probe beam;

measuring the nonmodulated power of the reflected pump beam; and processing the three reflected power measurements to derive the thickness of the amorphous material layer and thereafter correlating the derived thickness of the amorphous material layer to the implant dosage level in the semiconductor sample.

9. A method as recited in claim 8 further including the step of comparing the derived thickness of the amorphous material layer to the derived thickness of the amorphous material layer of other semiconductor samples having a known implant dosage level.

10. A method as recited in claim 8 wherein said semiconductor sample is formed from crystalline silicon and the amorphous material layer is amorphous silicon.

* * * * *